United States Patent
Kohn et al.

(10) Patent No.: US 8,414,871 B2
(45) Date of Patent: *Apr. 9, 2013

(54) CONTROLLED RELEASES OF ACTIVES IN SKIN

(75) Inventors: Joachim Kohn, Piscataway, NJ (US); Bozena Michniak, Piscataway, NJ (US); David Devore, Princeton, NJ (US); Larisa Sheihet, Monmouth Junction, NJ (US); Prafulla Chandra, Highland Park, NJ (US); Priya Batheja, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/525,529

(22) PCT Filed: Jan. 31, 2008

(86) PCT No.: PCT/US2008/052728
§ 371 (c)(1),
(2), (4) Date: Jul. 31, 2009

(87) PCT Pub. No.: WO2008/095144
PCT Pub. Date: Aug. 7, 2008

(65) Prior Publication Data
US 2009/0317472 A1    Dec. 24, 2009

Related U.S. Application Data

(63) Continuation-in-part of application No. 11/191,181, filed on Jul. 27, 2005, which is a continuation-in-part of application No. 10/514,215, filed as application No. PCT/US03/15600 on May 15, 2003, now abandoned.

(60) Provisional application No. 60/887,553, filed on Jan. 31, 2007, provisional application No. 60/378,042, filed on May 15, 2002.

(51) Int. Cl.
*A61K 8/72* (2006.01)

(52) U.S. Cl.
USPC ............... 424/70.11; 424/70.1; 424/78.02; 424/78.03

(58) Field of Classification Search .............. None
See application file for complete search history.

(56) References Cited

U.S. PATENT DOCUMENTS

| | | | |
|---|---|---|---|
| 5,658,995 A | | 8/1997 | Kohn et al. |
| 6,468,980 B1 * | | 10/2002 | Jariwalla ............ 514/34 |
| 6,475,477 B1 | | 11/2002 | Kohn et al. |
| 2003/0129151 A1 * | | 7/2003 | Candau et al. ........ 424/59 |
| 2006/0013882 A1 | | 1/2006 | Kohn et al. |

OTHER PUBLICATIONS

Galanski et al. "Searching for the Magic Bullet: Anticancer Platinum Drugs Which Can Be Accumulated or Activated in the Tumor Tissue" Anti-Cancer Agents in Medicinal Chemistry, 2007, 7, 55-73.*

* cited by examiner

*Primary Examiner* — James Rogers
(74) *Attorney, Agent, or Firm* — Fox Rothschild LLP

(57) ABSTRACT

Topical compositions are provided in which active compounds for topical delivery through the stratum corneum are complexed with nanospheres of a triblock copolymer having an A-B-A structure wherein each A end block is a water-soluble, hydrophilic and non-toxic polymer or oligomer; and the hydrophobic middle B block is a hydrophobic polymer or oligomer with the same or different repeating units having the structure according to formula:(I) wherein X is —C—R—C— or —C—; Z is between 2 and about 100, inclusive; $R_1$ is CH=CH or $(CH_2)_n$, wherein n is from 0 to 18, inclusive; $R_2$ is selected from hydrogen and straight and branched alkyl, alkoxy, alkylaryl and alkoxyaryl groups containing up to 18 carbon atoms; and R is selected from a bond or straight and branched alkyl, alkoxy, alkylaryl and alkoxyaryl groups containing up to 18 carbon atoms.

35 Claims, 6 Drawing Sheets

CONTROLLED RELEASES OF ACTIVES IN SKIN

CROSS REFERENCE TO RELATED APPLICATION

The present application is a 35 U.S.C. §371 National Phase application of International Application Serial No. PCT/US2008/52728 filed Jan. 31, 2008, which is a Continuation-In-Part of U.S. patent application Ser. No. 11/191,181 filed Jul. 27, 2005, which is a Continuation-In-Part of U.S. patent application Ser. No. 10/514,215 filed Nov. 7, 2005, which claims priority benefit under 35 U.S.C. §365(c) of International Application Serial No. PCT/US03/015600 designating the United States filed May 15, 2003, which claims priority benefit under 35 U.S.C. §119(e) of U.S. Provisional Patent Application Ser. No. 60/378,042 filed May 15, 2002. PCT/US08/52728 also claims priority benefit under 35 U.S.C. §119(e) of U.S. Provisional Patent Application No. 60/887,553 filed Jan. 31, 2007. The disclosures of all applications are incorporated herein by reference.

BACKGROUND OF THE INVENTION

The skin is a complex membrane that performs many physiological functions such as metabolism, synthesis, temperature regulation, and excretion. Its upper layer, the stratum corneum, is considered to be the main barrier to the percutaneous penetration of exogenous materials.

There are several categories of pharmaceutical products which are targeted to the skin or utilize the skin as a port of entry into the body. These include transdermal and topical drug delivery systems (patches), gels, creams, ointments, lotions, as well as subcutaneous implants and dermal vaccinations. As with other routes of delivery, transport into and across the skin is also associated with several disadvantages mainly that not all drugs are suitable candidates.

A number of physicochemical parameters have been identified, such as molecular hydrophobicity, size, and the ability to interact with the other molecules, e.g. hydrogen bond formation that influence the diffusion process, and variations in permeation rates can occur between different skin models, patients, different races, and between young and old. The major challenge is overcoming the resistance of the skin to perneation in a reversible and non-damaging manner, as well as the design of therapeutically effective topical and transdermal formulations.

The development of topical and transdermal drug delivery systems has been aimed at overcoming the remarkably efficient barrier property of human skin by nontoxic and non-irritant methods. Numerous chemical and physical approaches have been investigated to overcome the skin's formidable barrier function and can be divided into passive or active methods. Active methods of enhancing skin permeation include techniques such as iontophoresis (electrical approach), use of microneedles (mechanical approach), ultrasound, laser and photomechanical waves. Passive methods include use of penetration enhancers, liposomes, or other vehicles, prodrug or metabolic approach, enhancement of the driving force of drug diffusion (thermodynamic activity), and/or increasing the permeability of the skin.

The choice of formulation is also important in order to obtain a suitable profile in terms of solubility/dispersability and stability of the drug. The most functional formulation should be able to solubilise both hydrophobic and hydrophilic substances and at the same time increase uptake efficiency without causing notable damage to the skin. An additional challenge in topical delivery to the skin is the limited number of suitable drugs which are generally reduced to small, moderately lipophilic and highly potent ones. In general, highly lipophilic molecules do not transfer well from the mainly lipidic stratum corneum into the more aqueous viable epidermis and, as a result, are often poorly permeable.

Several strategies for improving cutaneous delivery, including complex physical enhancement methods, for example, iontophoresis, sonophoresis, and electroporation, have been developed, however these techniques are more suited to hydrophilic, water-soluble substances. With respect to passive enhancement methods, supersaturated formulations or novel vehicle systems, for example, microemulsions, liposomes, and colloidal polymeric suspensions, have also been investigated as alternatives to the more "classic" chemical penetration enhancer systems. A limited number of biodegradable, polymer microparticles and solid-lipid nanoparticles have been investigated with respect to their potential for transdermal drug administration. Nevertheless the percutaneous penetration of highly lipophilic molecules remains problematic and need for a suitable delivery vehicle is in demand.

SUMMARY OF THE INVENTION

This need is met by the present invention. Topical compositions are provided containing active compounds for topical delivery through the stratum corneum that are complexed with nanospheres of a triblock copolymer having an A-B-A structure wherein each A end block is a water-soluble, hydrophilic and non-toxic polymer or oligomer; and the middle B block is a hydrophobic polymer or oligomer with the same or different repeating units having a structure according to the formula:

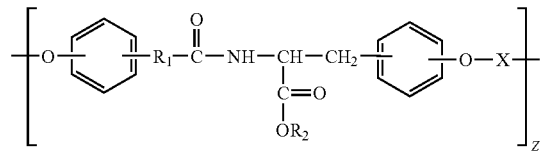

wherein X is

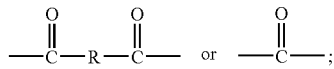

Z is between 2 and about 100, inclusive; $R_1$ is CH=CH or $(CH_2)_n$, wherein n is from 0 to 18, inclusive; $R_2$ is selected from hydrogen and straight and branched alkyl, alkoxy and alkylaryl groups containing up to 18 carbon atoms; and R is selected from a bond or straight and branched alkyl, alkoxy, alkylaryl and alkoxyaryl groups containing up to 18 carbon atoms.

According to one embodiment the topical compositions further comprise a pharmaceutically acceptable carrier. The pharmaceutically acceptable carrier may comprise one or more ingredients selected from diluents, solubilizers, lubricants, suspending agents, encapsulating materials, solvents, thickeners, dispersants, buffers, anti-oxidants, preservatives, carbohydrates, sugars, chelating agents, sugar alcohols, counter-ions and non-ionic surfactants. The pharmaceutically acceptable carrier may be formulated as an aqueous dispersion, emulsion, cream, ointment, gel-like or solid polymer matrix, or porous ceramic matrix.

The active compound may be hydrophilic or hydrophobic. In addition, the active compound may be a local or systemic drug. Examples of active compounds include antibiotics, antimicrobials, anti-acne agents, anti-tumor agents, non-steroidal anti-inflammatory agents (NSAIDS), antihistaminic agents, antitussives, antipruritic agents, anticholinergic agents, anti-emetic and antinauseant agents, anorexic agents, central stimulant agents, anti-arrhythmic agents, β-adrenergic blockers, cardiotonic agents, anti-hypertensives, diuretics, vasodilators, vasoconstrictor agents, anti-ulcer agents, anesthetic agents, antidepressants, tranquilizers and sedatives, antipsychotic agents, anti-microbial agents, antineoplastic agents, antimalarial agents, muscle relaxants and antidiarrheal agents.

Topical compositions according to the present invention in the form of personal care products are also provided, such as shampoos, hair conditioners, body washes, skin conditioners, deodorants, anti-perspirants, and the like in which the active compound is a shampoo, skin washing, hair or skin conditioning active ingredient or a deodorant or antiperspirant active ingredient. Other topical compositions according to the present invention for topical application to the skin are provided in which the active compound comprises is a sunless tanning agent, skin bleaching or lightening agent, moisturizing agent, or a UV-A or UV-B absorbing compound.

The present invention also provides cosmeceutical topical compositions containing one or more active compounds that are cosmeceutical ingredients. Examples of cosmeceutical ingredients include natural vitamins, minerals, natural oils, phytochemicals, enzymes, antioxidants, anti-ageing agents, alpha hydroxy acids, glycolic acid and salicylic acid.

Topical compositions are also provided for the treatment of skin diseases or disorders. Topical compositions according to this embodiment of the present invention contain one or more active compounds for the treatment of the disease or disorder. Examples of active compounds for the treatment of skin diseases or disorders include therapeutic agents for the treatment of parasitic infections, fungal infections, bacterial infections, viral infections, papulosquamous diseases, pigmentary disorders, cancers and cutaneous drug reactions.

Topical compositions according to the present invention may contain a dermal penetration enhancer. Examples of dermal penetration enhancers include fatty acids, fatty acid esters, fatty alcohols, terpenes, glycols and glycol esters, 1,3-dioxolanes, macrocylic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates and mixtures thereof.

The present invention also provides topical methods for the delivery of active compounds. According to one embodiment, a topical method of active compound delivery through the stratum corneum to the underlying epidermis and dermis is provided by topically applying to the stratum corneum of a patient with a disease or disorder in need of treatment an effective amount of the topical composition of the present invention, wherein the active compound of the topical composition is effective to treat the patient's disease or disorder.

According to one embodiment, the disease or disorder is a skin disease or disorder selected from parasitic infections, fungal infections, bacterial infections, viral infections, papulosquamous diseases, pigmentary disorders, cancers and cutaneous drug reactions and the active compound includes one or more therapeutic agents for the treatment of the skin disease or disorder.

The foregoing and other objects, features and advantages of the present invention are more readily apparent from the detailed description of the preferred embodiments set forth below, taken in conjunction with the accompanying drawings.

DETAILED DESCRIPTION OF THE PREFERRED EMBODIMENTS

Figure 1:
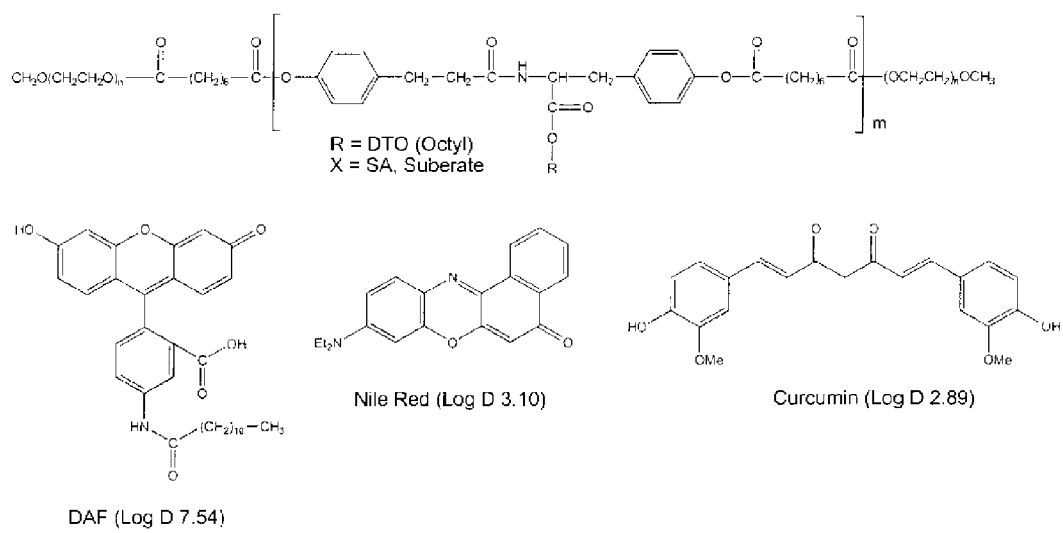
FIG. 1 is a representation of the structures of PEG-b-oligo (DTO-SA)-b-PEG triblock copolymer, 5-dodecanoylaminofluorescein (DAF), Nile Red, and Curcumin.

The present invention extends the application of tyrosine-based ABA-type triblock copolymer nanospheres, disclosed in United States Publication No. 2006/0013882, to delivery vehicles for active compounds for passive skin permeation.

The triblock copolymers are derived from water-soluble, hydrophilic, and non-toxic end blocks and a hydrophobic middle block of either a polyarylate or polycarbonate. The triblock copolymer has an A-B-A structure wherein each A end block is water-soluble, hydrophilic and non-toxic polymer or oligomer and the B middle block is a hydrophobic tyrosine-derived polycarbonate or polyarylate polymer or oligomer.

The triblock copolymers self-assemble spontaneously to form biocompatible, biodegradable nanospheres, which are useful for the delivery of drugs and other actives even at very low concentration. Accordingly, compositions are provided in which active compounds for topical delivery through the stratum corneum are complexed with nanospheres of a triblock copolymer having an A-B-A structure wherein each A end block is water-soluble, hydrophilic, and non-toxic; and the hydrophobic middle B block is hydrophobic with the same or different repeating units having the structure according to Formula (II):

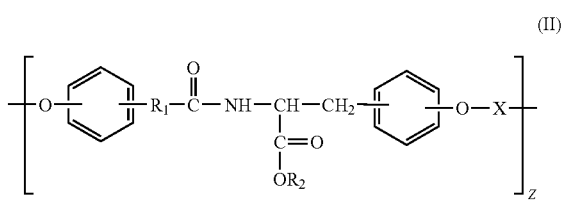

(II)

wherein X is

Z is between 2 and about 100, inclusive; $R_1$ is CH=CH or $(CH_2)_n$, wherein n is from 0 to 18, inclusive; $R_2$ is selected from hydrogen and straight and branched alkyl, alkoxy, alkylaryl and alkoxyaryl groups containing up to 18 carbon atoms; and R is selected from a bond or straight and branched alkyl, alkoxy, alkylaryl and alkoxyaryl groups containing up to 18 carbon atoms.

The copolymers of the present invention are A-B-A type triblocks. The A end blocks are water-soluble, hydrophilic, and non-toxic, preferably selected from poly(alkylene oxides), and the hydrophobic middle B block is either a polyarylate or polycarbonate. In a preferred polyarylate embodiment, the mid-block is copolymerized from a tyrosine-derived diphenol and a diacid, linked together by an ester bond between the phenolic hydroxyl group of the tyrosine-derived diphenol and the carboxylic acid group of the diacid. In another preferred embodiment, the polycarbonate mid-block is copolymerized from the same dihydroxy monomers.

Among the more preferred poly(alkylene oxides) end blocks are polyethylene glycol, polypropylene glycol, polybutylene glycol, Pluronic™ polymers, and the like. Polyethylene glycols are preferred.

The polyarylate middle blocks of the present invention are prepared by condensation of a diacid with a diphenol according to the method described by U.S. Pat. No. 5,216,115 in which diphenol compounds are reacted with aliphatic or aromatic dicarboxylic acids in a carbodiimide mediated direct polyesterification using 4-(dimethyl-amino)-pyridinium-p-toluene sulfonate (DPTS) as a catalyst. The disclosure of U.S. Pat. No. 5,216,115 in this regard is incorporated herein by reference. Bis-diacids are selected as the polyarylate middle blocks to permit the A end blocks to be coupled at each end of the copolymer.

The diphenol compounds are the tyrosine-derived diphenol monomers of U.S. Pat. Nos. 5,587,507 and 5,670,602, the disclosures of both of which are also incorporated herein by reference. The polyarylates are prepared using tyrosine-derived diphenol monomers having the structure of Formula III:

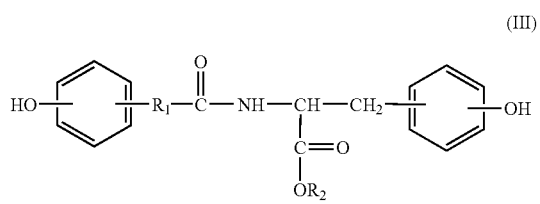

(III)

wherein $R_1$ and $R_2$ are the same as described above with respect to Formula II.

The preferred diphenol monomers are desaminotyrosyl-tyrosine carboxylic acids and esters thereof, wherein $R_1$ is —$CH_2$—$CH_2$—, which are referred to as DT esters. For purposes of the present invention, the ethyl ester ($R_2$=ethyl) is referred to as DTE, the benzyl ester ($R_2$=benzyl) as DTBn, and so forth. Both patents disclose methods by which these monomers may be prepared. For purposes of the present invention, the desaminotyrosyl-tyrosine free carboxylic acid ($R_2$=hydrogen) is referred to as DT.

The polyarylate dicarboxylic acids have the structure:

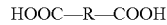

wherein R is the same as described above with respect to Formula II, and preferably contains up to 12 carbon atoms. R is preferably selected so that the dicarboxylic acids employed as starting materials are either important naturally-occurring metabolites or highly biocompatible compounds. Preferred Formula IV dicarboxylic acids therefore include the intermediate dicarboxylic acids of the cellular respiration pathway known as the Krebs cycle. These dicarboxylic acids include alpha-ketoglutaric acid, succinic acid, fumeric acid, malic acid, and oxaloacetic acid, for which R is —$CH_2$—$CH_2$—C(=O)—, —$CH_2$—$CH_2$—, —CH=CH—, —$CH_2$—CH(—OH)— and —$CH_2$—C(=O)—, respectively.

Another naturally-occurring, preferred dicarboxylic acid is adipic acid (R=(—$CH_2$—)$_4$), found in beet juice. Other preferred biocompatible dicarboxylic acids include oxalic acid (no R), malonic acid (R=—$CH_2$—), glutaric acid (R=(—$CH_2$—)$_3$, pimellic acid (R=(—$CH_2$—)$_5$), suberic acid (R=(—$CH_2$—)$_6$) and azalaic acid (R=(—$CH_2$—)$_7$). In other words, among the dicarboxylic acids suitable for use in the present invention are compounds in which R represents (—$CH_{12}$—)$_z$, wherein z is an integer between 0 and 12, inclusive. A preferred class of highly biocompatible aromatic dicarboxylic acids are the bis(p-carboxyphenoxy) alkanes such as bis(p-carboxyphenoxy) propane.

The polyarylate triblock oligomers are synthesized in a one pot reaction using in situ carbodiimide coupling of a non-functionalized poly(alkylene oxide) monoalkyl ether and oligo (DTO suberate). The following is a specific example of this general design, illustrating the synthesis of PEG-oligo-(DTO suberate)-PEG:

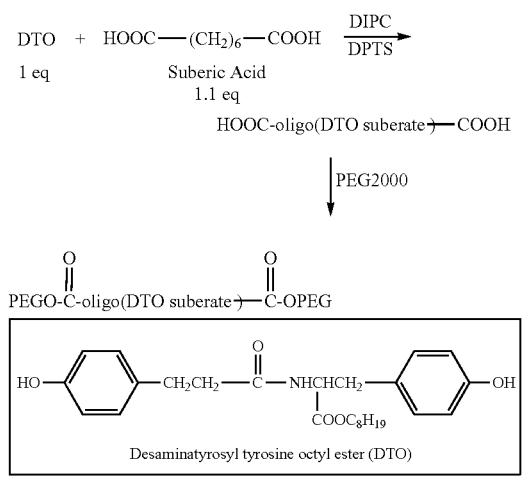

The polycarbonate middle blocks of the present invention can be prepared by the conventional methods for polymerizing diphenols into the same, as described by U.S. Pat. No. 5,099,060 the disclosure of which is incorporated herein by reference. These methods involve the reaction of amino acid-derived diphenol compounds, including those described in U.S. Pat. No. 4,980,449, the disclosure of which is incorporated herein by reference, with phosgene or phosgene precursors (e.g. diphosgene or triphosgene) in the presence of a catalyst. Suitable processes, associated catalysts, and solvents are known in the art and are taught in Schnell, *Chemistry and Physics of Polycarbonates* (Interscience, New York 1964), the teachings of which are incorporated herein by reference.

It is not possible to polymerize oligomers having pendant free carboxylic acid groups from diphenols with pendant free carboxylic acid groups without cross-reaction of the free carboxylic acid groups with the co-monomer. Accordingly, homopolymers or copolymers of benzyl ester diphenyl monomers such as DTBn may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491. The disclosure of this patent is incorporated by reference. The catalytic hydrogenolysis is necessary because the lability of the oligomer backbone prevents the employment of harsher hydrolysis techniques. Another method, disclosed by co-pending and commonly owned U.S. patent application Ser. No. 10/952,202, involves the selective removal of tert-butyl ester groups from a hydrolytically unstable polymer to form a new polymer composition having free carboxylic acid groups in place of the tert-butyl ester groups. The disclosure of this application is also incorporated by reference.

The molecular weights of the triblock copolymers can be controlled either by limiting the reaction time or the ratios of the components. Molecular weights can also be controlled by the quantity of the carbodiimide coupling reagent that is used.

Preferred polyarylates have weight average molecular weights between about 1,000 and 100,000 g/mol, preferably between about 3,000 and 50,000 g/mol, and more preferably between about 10,000 and 25,000 g/mol. Molecular weights are calculated by gel permeation chromatography relative to polystyrene standards in tetrahydrofuran without further correction. The triblock copolymers thus have weight average molecular weights between about 2,500 and 130,000 g/mol, preferably between about 5,000 and 80,000 g/mol, and more preferably between about 10,000 and 50,000 g/mol.

Preferred polycarbonates in accordance with the present invention have weight-average molecular weights ranging between about 1,000 and 100,000 g/mol, preferably between about 3,000 and 50,000 g/mol, and more preferably between about 10,000 and 25,000 g/mol. Molecular weights are calculated by gel permeation chromatography relative to polystyrene standards in tetrahydrofuran without further correction. The triblock copolymers thus have weight average molecular weights between about 2,500 and 130,000 g/mol, preferably between about 5,000 and 80,000 g/mol, and more preferably between about 10,000 and 50,000 g/mol.

The triblock copolymers degrade by hydrolysis into the original starting materials, i.e., the tyrosine-derived diphenols, the dicarboxylic acids, and the water-soluble, hydrophilic, and non-toxic oligomer end blocks. The inventive copolymers are highly hydrophilic, which is advantageous for nanosphere drug delivery systems. However, the hydrophilic:hydrophobic balance of the copolymers can be varied in several ways. The ester of the pendant chain of the diphenol can be changed, with longer-chain ester groups increasing hydrophobicity. Increasing the molecular weight of the A end blocks, for example, by increasing the number of carbons in the alkylene group of a poly(alkylene oxide) will also increase hydrophobicity. Changing the dicarboxylic acid will also change the hydrophilic:hydrophobic balance.

The triblock copolymers of the present invention form vesicular structures in dilute aqueous solutions in the 5-200 nm range (diameter). Preferred structures have diameters between 50 and 150 nm. For example, poly(ethylene glycol)-block-oligo-(DTO suberate)-block-poly(ethylene glycol), i.e., PEG-oligo-(DTO suberate)-PEG triblock oligomer, forms vesicular structures in dilute aqueous solution having a diameter of about 100 nm range. The vesicles are characterized with conventional techniques, i.e., light scattering.

The delivery systems of the present invention are suitable for applications where localized delivery is desired, as well as in situations where systemic delivery is desired. The nanospheres can be administered with or without being complexed with an active compound to provide a therapeutic effect.

The term "active compound" includes hydrophobic and hydrophilic compounds. The triblock copolymers thus can be used to form nanosphere hydrophobic drug delivery systems. The synthesis of triblock copolymers comprised of non-cytotoxic and biodegradable building blocks and capable of forming nanospheres by a self-assembly process is important for use in many biomedical applications including but not limited to the use as a carrier for hydrophobic drugs. For purposes of the present invention, a hydrophobic active agent is defined as an active agent, such as a drug or other biologically active material, having a log P>0 relative to octanol, wherein P is the partition coefficient.

It is well established that the self-assembly of amphiphilic molecules depends on several correlated properties of the underlying material, i.e., its chemical structure, architecture or molecular weight. However, assuming that the driving force of the self-assembly is mainly governed by hydrophobic interactions, the design of a self-assembling block copolymer inherently depends on its molecular weight and hydrophobic to hydrophilic balance. The self-assembly of the triblock copolymers in dilute aqueous solution is induced by simple dropwise addition and may be facilitated by sonication, high shear mixing, nanoprecipitation or emulsification methods. Active hydrophobic products are complexed by premixing the triblocks and hydrophobic products in suitable solvent prior to nanosphere formation or by forming the nanospheres in solutions or suspensions of the product to be complexed.

The nanosphere complexes of the present invention are topically applied employing a variety of dosage forms that may optionally include one or more carriers suitable for topical dosage forms. The tyrosine-derived polymeric self-assembling nanospheres of the present invention are able to permeate the stratum corneum and distribute within human skin layers. These nanospheres are capable of encapsulating active compounds, for example hydrophobic drugs, and delivering them to the epidermis and the dermis. Therefore the present invention also includes methods of drug delivery through the stratum corneum to the epidermis and the dermis by means of topical application of hydrophobic or hydrophilic active compounds encapsulated by nanospheres of the present invention. The compositions and methods of treatment have utility in both veterinary and human medicine and may be administered, in addition to human patients, to mammals and other animals such as birds, fish, reptiles and amphibians.

The active compounds may be inactive until separated from the nanosphere complexes, or it may remain within the nanosphere and be active in that form. For example, UV-A and UV-B absorbing compounds used as active ingredients in sun blocks and sun screens can remain complexed with nanospheres and absorb harmful UV radiation at the site to which they are applied.

Acceptable topical pharmaceutical carriers for therapeutic use are well known in the pharmaceutical field, and are described, for example, in *Remington's Pharmaceutical Science*, Mac Publishing Co., (A. R. Gennaro edt. 1985). Such materials are non-toxic to recipients at the dosages and concentrations employed, and include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin or immunoglobulins, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium and/or non-ionic surfactants such as Tween™, Pluronics™, or PEG. In one embodiment, for delivery through the stratum corneum to the epidermis and dermis, the nanosphere complexes are contained in an aqueous dispersion, an emulsion, cream, ointment, gel-like or solid polymer matrix, or porous ceramic matrix.

Nanospheres encapsulating a hydrophobic agent to be delivered may also be dispersed as a reservoir of the agent within the oligomeric matrix of controlled release device. The host oligomeric matrix may be a hydrogel or other bioerodible oligomer. Such dispersions would have utility, for example, as active agent depots in transdermal drug delivery devices.

The nanosphere complexes can be delivered with or without the use of physical and/or chemical enhancement methods for skin delivery. Suitable methods of physical enhancement include thermal energy, ultrasound including phonophoresis and sonophoresis, magnetophoresis, photochemical waves and laser ablation, radio frequency energy, pulsed electric fields, electrophoresis, iontophoresis, microscissioned microconduits, membrane electroporation, solid or hollow microneedles, puncture, perforation, abrasion, needless injection, suction, and stretching. Chemical enhancement includes the use of fatty acids, fatty acid esters, fatty alcohols, terpenes, glycols and glycol esters, 1,3 dioxolanes, macrocylic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters and mixtures thereof. More preferably the dermal penetration enhancer is selected from the list including oleic acid, oleyl alcohol, cyclopentadecanone (CPE-218™), sorbitan monooleate, glycerol monooleate, propylene glycol monolaurate, polyethylene glycol monolaurate, 2-n-nonyl 1,3-dioxolane (SEPA™), dodecyl 2-(N,N-dimethylamino)-proprionate (DDAIP) or its salt derivatives, 2-ethylhexyl 2-ethylhexanoate, isopropyl myristate, dimethyl isosorbide, 4-decyloxazolidinon-2-one (SR 38™, TCPI, Inc.), 3-methyl-4-decyloxazolidinon-2-one, octyl dimethyl-para-aminobenzoate, octyl para-methoxycinnamate, octyl salicylate and mixtures thereof.

The delivery system and its method of preparation are particularly well suited for use with active compounds such as pharmacologically active proteins, macromolecules, peptides, vaccines, nucleic acids, including plasmids, oligonucleotides, and SiRNA, and the like, as well as with other hydrophilic and hydrophobic small pharmacologically active molecules and contrast agents. Suitable active compounds include, but are not limited to, synthetic and natural drugs, antibiotics, antimicrobials, anti-acne agents, anti-tumor agents, non-steroidal anti-inflammatory agents (NSAIDS), antihistaminic agents, antitussive agents, antitussive agents, antipruritic agents, anticholinergic agents, anti-emetic and antinauseant agents, anorexic agents, central stimulant agents, antiarrhythmic agents, β-adrenergic blocker agents, cardiotonic agents, antihypertensive agents, diuretic agents, vasodilator agents, vasoconstrictor agents, anti-ulcer agents, anesthetic agents, antidepressant agents, tranquilizer and sedative agents, antipsychotic agents, antimicrobial agents, antineoplastic agents, antimalarial agents, muscle relaxant agents, antidiarrheal agents, sunless tanning agents, skin bleaching (or lightening) agents, cosmetics, products that combine drug and cosmetic properties ("cosmeceuticals"), including natural vitamins, minerals, and oils, phytochemicals, enzymes, antioxidants, anti-ageing agents, keratolytics (alpha hydroxy acids, glycolic acid and salicylic acid), and moisturizing agents, skin cleaners, hair cleaners, deodorants, shampoos, conditioners, colorants, sunburn preventatives and treatments, and therapeutic agents for treatment of skin diseases including parasitic, fungal, bacterial, and viral infections, papulosquamous diseases, pigmentary disorders, cancers and cutaneous reactions to drugs.

Exemplary active compounds include salicylic acid, sulfur, lactic acid, glycolic, pyruvic acid, urea, resorcinol, N-acetylcysteine, retinoids for example retinoic acid and its derivatives (e.g., cis and trans), antibiotics and antimicrobials such as benzoyl peroxide, octopirox, erythromycin, tetracyclin, triclosan, azelaic acid and its derivatives, phenoxy ethanol and phenoxy proponol, ethylacetate, clindamycin, meclocycline, sebostats such as flavinoids, hydroxy acids, bile salts for example scymnol sulfate and its derivatives, deoxycholate, cholate, propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, steroidal anti-inflammatory drugs including hydrocortisone and the like, triprolidine, diphenhydramine, doxylamine, pyrilamine, phenindamine, promethazine, cyproheptadine, azatadine, clemastine, carbinoxamine, tripelennamine, terfenadine, dexchlorpheniramine, brompheniramine, chlorcyclizine, diphenylpyraline, pheniramine, phenyltoloxamine, dextromethorphan, codeine, caramiphen, carbetapentane, methdilizine, trimeprazine, scopolamine, atropine, homatropine, levodopa, dicyclomine, hyoscyamine, procyclidine, trihexyphenidyl, ethopropazine, cyclizine, meclizine, chlorpromazine, buclizine, metoclopramide, prochlorperazine, trimethobenzamide, benzphetamine, phentermine, chlorphentermine, fenfluramine, diethylpropion, phendimetrazine, amphetamine, methamphetamine, dextroamphetamine, methylphenidate, propranolol, procainamide, disopyramide, quinidine, encainide, flecanaide, mexiletine and tocainide, salts of 3S-hydroxy-10,11-dihydroquinidine, 3R-hydroxy-10,11-dihydroquinidine, 3R-hydroxy-O-acetyl-10,11-dihydroquinidine, 3S-hydroxy-O-acetyl-10,11-dihydroquinidine, especially 3S-hydroxy-10,11-dihydroquinidine, metoprolol, acebutolol, betaxolol, labetalol, timolol, metoprolol tartrate, acebutolol hydrochloride, betaxolol hydrochloride, labetalol hydrochloride, timolol maleate, salts of milrinone, amrinone, dobutamine, 14-amino steroid derivatives, salts of enalapril, clonidine, hydralazine, minoxidil (which is also a hair growth stimulator drug), guanadrel, guanethidine, guanfacine, mecamylamine, methyldopate, pargyline, phenoxybenzamine, prazosin, amiloride, hydrochlorothiazide, diltazem, amiodarone, isoxsuprine, nylidrin, tolazoline, verapamil, dihydroergotamine, ergotamine, methysergide, ranitidine, cimetidine, lidocaine, bupivacaine, chlorprocaine, dibucaine, etidocaine, mepivacaine, tetracaine, dyclonine, hexylcaine, procaine, cocaine, ketamine, pramoxine, phenol, imipramine, desipramine, amitriptyline, nortriptyline, protriptyline, doxepin, maprotiline, phenelzine, tranylcypromine, trazodone, trimipramine, chlordiazepoxide, benactyzine, benzquinamide, flurazepam, hydroxyzine, loxapine, promazine, chlorprothixene, fluphenazine, haloperidol, molindone, thioridazine, trifluoperazine, β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole, amanfadine, tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate, clotrimazole, bleomycin, daunorubicin, doxorubicin, mechlorethamine, procarbazine, quinacrine, tamoxifen, vinblastine, vincristine, chloroquine, hydroxychloroquine primaquine, quinine, cinnamedrine, cyclobenzaprine, flavoxate, orphenadrine, papaverine, mebeverine, idaverine, ritodrine, dephenoxylate, dantrolene, azumolene, loperamide, dihydroxyacetone, indole derivatives, and the like, hydroquinone, ascorbic acid, kojic acid, and sodium metabisulfite.

Disorders suitable for treatment with the nanosphere complexes of the present invention include, but are not limited to, systemic diseases, for example, acrodermatitis enteropathica, acrodynia, acute febrile neutrophilic dermatosis, amyloidosis, angioedema, annular erythema, antiphospholipid syndrome, argyria, Behcet disease, biotin-responsive dermatoses, calciphylaxis, carotenaemia (carotenemia), chilblains, chloracne, connective tissue diseases, Crohn disease, cryoglobulinaemia, cushing syndrome, cutaneous markers of malignancy, Degos disease, dermatitis herpetiformis, dermatomyositis, diabetes, diabetic foot ulcers, down syndrome, drug eruptions, Ehler Danlos syndrome, eosinophilic fasciitis, erythema multiforme, erythema nodosum, Eerythropoeitic protoporphyria, flushing, glucagonoma, Gorlin syndrome, graft versus host disease, granuloma annulare, haemochromatosis, histiocytoses, hypereosinophilic syndrome, incontinentia pigmenti, iron deficiency, itch, job syndrome, Kwashiorkoar, LEOPARD syndrome, livedo reticularis, Lupus erythematosus, lyme disease, Marfan syndrome, mastocytosis, menopause, morphoea, mucinoses, myxoma syndrome, necrobiosis lipoidica, necrolytic migratory erythema, panniculitis, PAPA syndrome, photosensitivity, polyarteritis nodosa, polymorphous eruption of pregnancy, porphyria cutanea tarda, pretibial myxoedema, Prurigo nodularis, Proteus syndrome, pruritus, pseudoxanthoma elasticum, pyoderma gangrenosum, Reiter syndrome, reticular erythematous mucinosis, rheumatoid arthritis, SAPHO syndrome, sarcoidosis, scleroderma (localised), scleredema, scleromyxoedema, Scurvy, Sézary syndrome, Sjögren syndrome, skin cancer in transplant recipients, stoma skin problems, sweet disease, systemic sclerosis, telogen effluvium, thyroid disease, toxic epidermal necrolysis, tuberous sclerosis, urticaria, vasculitis, Wegener granulomatosis, Wells syndrome, Wilson disease, xanthomas, xeroderma pigmentosum, lesions, tumors and cancers, acne/follicular diseases, eczema, dermatitis and allergies, blistering diseases, immunological disorders, scaly skin diseases, erosions & ulcers, vascular skin problems, pigmentation problems, pruritus (itch), reactions to external agents, actinic keratoses, aging skin, angiokeratoma, angiosarcomas, aplasia cutis, atypical fibroxanthoma, atypical naevi, basal cell carcinoma, Bazex syndrome (acrokeratosis neoplastica), Bazex syndrome (follicular atrophoderma-basal cell carcinoma), Becker naevus, birthmarks, blue naevus, Bowen's disease (non-genital), Bowen's disease of penis, Bowen's disease of vulva, brown spots & freckles, chilblains, chondrodermatitis nodularis, clear-cell acanthoma, comedone naevus, congenital melanocytic naevi, corns & calluses, cutaneous B-cell lymphoma, cutaneous T-cell lymphoma, dermatofibroma (histiocytoma), dermatofibrosarcoma protuberans, epidermal naevi, epidermoid cysts, eruptive keratoacanthomas, extramammary Paget disease, disseminated superficial actinic, porokeratosis, erythroplasia of Queyrat Gorlin's syndrome, Grzybowski syndrome, haemangioma, halo moles, infantile digital fibroma, inflammatory linear verrucous epidermal naevus, juvenile xanthogranuloma, Kaposi sarcoma, keloids and hypertrophic scars, keratoacanthoma, lentigines, lentigo simplex, lichenoid keratosis, linear porokeratosis, lipoma, melanoma, Merkel cell carcinoma, metastases, Meyerson naevus, moles, Mongolian spot, morphoea (localised scleroderma, morphea), mucous (myxoid) cyst, mycosis fungoides, naevi, naevi (nevi) of Ota & Ito, necrobiosis lipoidica, neuronfibromas, Paget disease, penile intraepithelial neoplasia, pilomatricoma, pyogenic granuloma, sebaceous cysts, sebaceous hyperplasia, sebaceous naevus, seborrhoeic keratoses, Sezary syndrome, skin cancer, skin metastasis, skin tags, solar (senile) comedones, solar keratoses, Spitz naevi, squamous cell carcinoma, squamous cell papilloma, steatocystoma multiplex, syringoma, trichoepithelioma, trichofolliculomas, trichostasis spinulosa, vulvar intraepithelial neoplasia, vulvar cancer Xanthogranuloma, eczema, dermatitis, allergies, allergic contact dermatitis, angioedema, atopic dermatitis (atopic eczema), atopic dermatitis, atopic dermatitis complications, autoeczematisation, chronic actinic dermatitis, cradle cap, dermatitis, dermatitis herpetiformis, dermographism, discoid eczema, dry skin, dust mite, dyshidrosis, eczema, eczema craquele, exfoliative keratolysis, fixed drug eruption, gravitational eczema, hand dermatitis, intertrigo, irritant contact dermatitis, juvenile plantar dermatosis, lichen simplex, lichen striatus, napkin dermatitis, nummular dermatitis, otitis externa, papular urticaria, patch tests, perioral dermatitis, photocontact dermatitis, photosensitivity, photosensitivity dermatitis, phototesting, pityriasis alba, polymorphic light eruption, polymorphous eruption of pregnancy, pompholyx, prurigo nodularis, pruritus ani, pruritus vulvae, Seborrhoeic dermatitis, urticaria, winter itch, blistering diseases, dermatitis herpetiformis, Hailey-Hailey (familial pemphigus), bullous pemphigoid, cicatricial pemphigoid, epidermolysis bullosa acquisita, epidermolysis bullosa, linear IgA dermatosis, paraneoplastic pemphigus, pemphigoid gestationis, pemphigus foliaceus, pemphigus vulgaris, blistering skin infections, chickenpox (varicella), erysipelas, hand foot & mouth disease, herpes simplex, herpes zoster (shingles), impetigo, scabies, staph, scalded skin syndrome, eczema, dyshidrosis (pompholyx), discoid (nummular) eczema, plant dermatitis, immunological disorders, blistering diseases, connective tissue diseases, dermatitis, disorders affecting hair, nails, and sweating, lichen planus, lichen sclerosus, psoriasis, scaly skin diseases, acquired keratoderma, actinic (solar) keratoses, BCC (superficial), Bowen's disease (squamous cell carcinoma in situ), chronic superficial scaly dermatosis (parapsoriasis), cracked heels, cradle cap, cutaneous T-cell lymphoma, Darier disease, dermatitis (Eczema), collodion baby, confluent and reticulated papillomatosis, diffuse hereditary keratoderma, disseminated superficial actinic porokeratosis, dry skin, erythrasma, exfoliative keratolysis, focal hereditary keratoderma, fungal infections, Grover's disease, ichthyosis, juvenile plantar dermatosis, keratoderma, Kyrle disease, lichen striatus, lupus erythematosus, Netherton syndrome, palmoplantar keratoderma, pellagra, pityriasis alba, pityriasis lichenoides, pityriasis rosea, pityriasis rotunda, pityriasis rubra pilaris, pityriasis versicolor, psoriasis, punctate keratoderma, Reiter syndrome, Seborrhoeic dermatitis, subcorneal pustular dermatosis (Sneddon Wilkinson disease), tinea infections, erosions and ulcers, trauma, Stasis/varicose/venous ulcers, Pressure ulcers, Hypertensive leg ulcers, Arteriosclerotic ulcers, Neuropathic ulcers eg diabetic, Ulcerating skin cancers (BCC, SCC, Melanoma), Panniculitis, Vasculitic ulcers, cutaneous polyarteritis nodosa, Pyoderma gangrenosum, Wegener granulomatosis, bacterial, viral or fungal infections in immune suppressed, mycosis fungoides, spider bites, atypical mycobacterial infections, genital infections, Porphyria cutanea tarda, Erythropoeitic protoporphyria, wounds in general, Chondrodermatitis nodularis helices, erosive pustular dermatosis, Aphthous ulcers (mouth & genitals), Aplasia cutis; vascular skin problems, angioma serpiginosum, angiosarcomas, Ataxia-telangiectasia, blushing, capillaritis, pigmented purpura, Schamberg disease, capillary vascular, malformations (portwine stain, salmon patch), cutaneous vasculitis, cutis marmorata, erythema elevatum diutinum, erythromelalgia, essential telangiectasia, haemangioma (hemangioma, strawberry birthmark), hereditary haemorrhagic telangiectasia, Kaposi sarcoma, lymphoedema, Poikiloderma of Civatte, polyarteritis nodosa, purpura, pyogenic granuloma, rosacea, steroid rosacea, telangiectasia macularis eruptiva perstans, urticarial vasculitis, venous malformations (including glomus tumours), vasculitis, and pigmentation problems.

Therapeutically effective dosages may be determined by either in vivo or in vitro methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each active compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the active compound from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

The nanosphere-drug complexes of this invention may be prepared for storage under conditions suitable for the preservation of drug activity as well as maintaining the integrity of the copolymers, including lyophilization, and are typically suitable for storage at ambient or refrigerated temperatures. Sterility may be readily accomplished by conventional methods.

The following non-limiting examples set forth hereinbelow illustrate certain aspects of the invention. All parts and percentages are by weight unless otherwise noted and all temperatures are in degrees Celsius.

EXAMPLES

Example 1

Preparation of Polymer and Nanosphere-Solute Formulations

Chemicals: Methylene chloride (HPLC grade), methanol (HPLC grade), 2-propanol and optimal cutting temperature compound (OCT) were purchased from Fisher Scientific, (Pittsburgh, Pa.). Suberic acid, 4 dimethylaminopyridinium-p-toluene sulfate (DMPTS), curcumin, propylene glycol (PG), poly(ethylene glycol) monomethyl ether (Mw 5000) and Dulbecco's phosphate buffered saline (PBS, pH 7.4) were purchased from Aldrich Chemical Co. (Milwaukee, Wis.). Diisopropylcarbodiimide (DIPC) was purchased from Tanabe Chemicals (San Diego, Calif.). N,N-dimethylformamide (DMF) and tetrahydrofuran (THF) were obtained from Merck (EM Science, Darmstadt, Germany), and dimethyl sulfoxide (DMSO) was obtained from Merck and Sigma. 5-Dodecanoylaminofluorescein (DAF) and Nile Red were obtained from Molecular Probes (Eugene, Oreg.). All reagents were used as received.

Polymer preparation and characterization: The triblock copolymer was synthesized in a one-pot reaction at 20° C. using in situ carbodiimide coupling of the PEG and oligo (DTO-SA) as described in U.S. Publication No. 2006/0013882, the contents of which are incorporated herein by reference. The chemical structure and purity of the copolymer was confirmed by $^1$H NMR (d6-DMSO, Varian Unity 300 spectrophotometer, Palo Alto, Calif.). Molecular weights (Mn and Mw) were determined using gel permeation chromatography, GPC (PL-gel columns, pore size 105 and 104 Å, Perkin-Elmer, Shelton, Conn.; Waters 410 RI detector) with 1 mL/min THF flow rate and polystyrene standards as Mw markers. The general chemical structure of the tyrosine-based triblock copolymer is illustrated in FIG. 1.

Preparation of Nanosphere-Solute Formulations: Nanosphere Complexes with or without solute compounds were prepared by combining 60 mg of triblock copolymer with 600 µg of either DAF or curcumin or Nile Red in 600 µL of DMF. These solutions were added drop-wise to 14.4 mL of deionized water with constant stirring. In order to remove particles greater than 220 nm in diameter, the resulting turbid aqueous dispersions were filtered through 0.22 µm PVDF syringe filters (Millipore, Bedford, Mass.), and the filtrate was used for all subsequent characterizations.

We refer to purified nanospheres as those that were processed as follows: the self-assembled nanosphere-solute suspensions were filtered through 0.22 μm filters; the filtered suspensions were isolated by ultracentrifugation of 12.25 mL nanosphere solutions at 65 000 rpm (290 000×g) for 3 h at 25° C. (Beckman L8-70M ultracentrifuge, Beckman Coulter, Fullerton, Calif.), followed by removal of the supernatant; the pelleted nanospheres were then washed twice with water, and re-suspended with gentle agitation in 1 mL of water at 25° C. Then, the volume of the re-suspended pellets was increased to 3 mL by the addition of water, and finally, the solutions were again filter-sterilized (0.22 μm).

Example 2

Characterization of Nanosphere-Solute Formulations

Size, size distribution, and morphology: The hydrodynamic diameter of the nanospheres was obtained by dynamic light scattering at q=90°, l=523 nm and T=298K using cumulant fit analysis (Lexel argon ion laser (Fremont, Calif.); Brookhaven Instruments goniometer and correlator BI-2030; Holtsville, N.Y.).

The morphology of nanospheres was determined using Transmission Electron Microscopy (TEM). For the negative staining experiments, a drop of the nanosphere dispersion was allowed to settle on a Formvar pre-coated grid for 1 min. The excess sample was removed by gentle blotting with filter paper and a drop of staining solution (2% uranyl acetate) was allowed to contact the sample for 1 min. Then, the excess stain was removed carefully by touching the grid edge to the edge of a filter paper wedge. For the Pt/C shadow method experiments, a drop of nanospheres was applied onto a copper Formvar/Carbon coated grid for ~1 min. Excess fluid was removed by gently blotting the grid with the edge of a torn piece of filter paper. The grids were air-dried and shadowed with 2.5 nm Pt/C (30°) using High Vacuum Freeze-Etch unit BAF 300 (Balzers, Elgin, Ill.). Electron micrographs were taken on a model JEM 100CX Transmission Electron Microscope (JEOL LTD, Peabody, Mass.).

Figure 2:
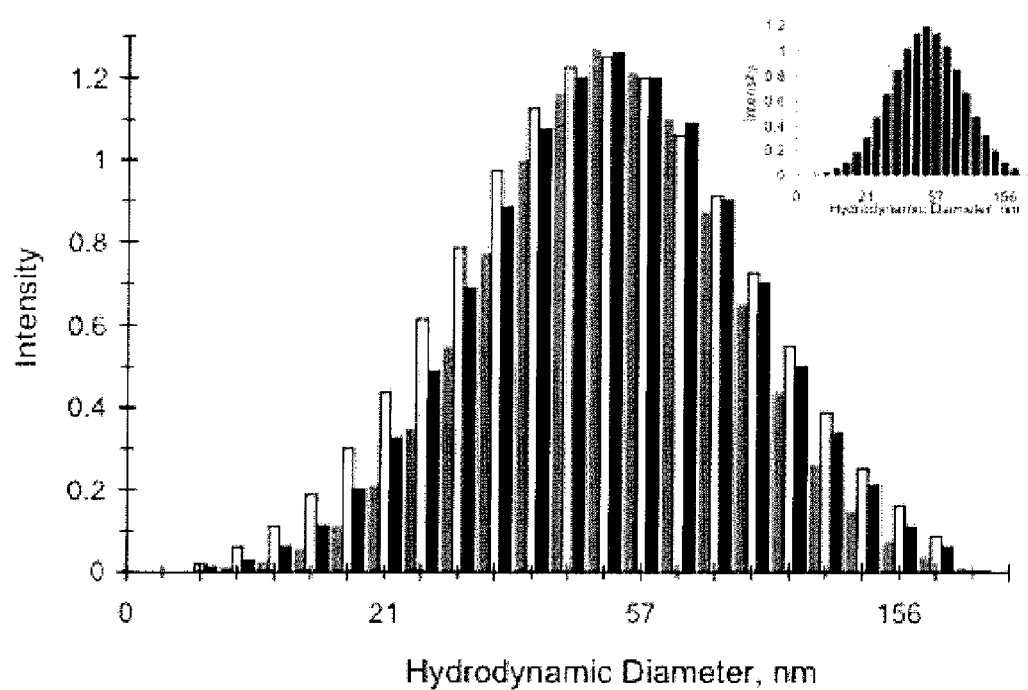
FIG. 2 is a graph depicting the size distribution of solute-nanosphere formulations as measured by dynamic light scattering (Cumulant fit). (v) nanosphere-Nile Red; (□) nanosphere-DAF complexes; (v) nanosphere-curcumin complexes. The insert: The size distribution of nanospheres alone.
Figure 3:
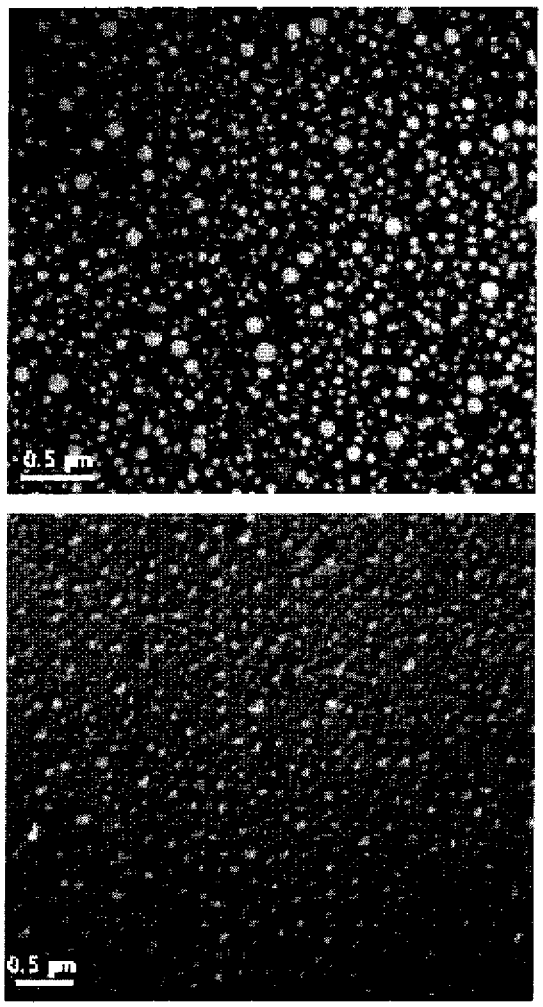
FIG. 3 includes Transmission Electron Microscopy (TEM) images of nanospheres made of PEG-b-oligo(DTO-SA)-b-PEG triblock copolymer in aqueous solution. Top: negative staining method (2% uranyl acetate); bottom: Pt/C shadow method.

The size distributions of nanosphere-solute complexes are shown in FIG. 2 The hydrodynamic diameters of the nanospheres prepared in the absence (the insert graph) or presence of different solutes have relatively narrow size distribution centered at 55 nm, indicating that neither the presence of solute in the nanospheres preparation nor the solute hydrophobicity have a significant effect on nanosphere size. FIG. 3 shows transmission electron micrographs obtained by negative staining using 2% uranyl acetate stain and by the Pt/C shadow method. These images represent spherical morphology of the nanospheres, however their size distribution appears to be larger than observed by light scattering analysis, ranging from 30 to 200 nm in diameter. This difference may be due to drying during the preparation of specimens for electron microscopy, which may have led to shrinkage and/or agglomeration of the nanospheres. Assuming that the average width of transepidermal hydrophilic pathways is in order of 0.4 (water evaporation pathways) to ~100 nm (intercorneocyte space), the relatively small size of tyrosine-derived nanospheres will easily allow their penetration into the stratum corneum along the surface furrows on the skin.

Solute binding efficiency: Sensitive, specific and reproducible HPLC methods were developed and validated for quantitative determination of DAF, Nile Red and curcumin in the copolymer system. The concentrations of the solutes were assayed by high-performance liquid chromatography (HPLC) using a Waters 2695 HPLC system equipped with UV/vis detector (Waters 2487, Dual 1 Absorbance Detector). Chromatographic separations were achieved using a RP-C18 column (Perkin-Elmer Brownlee Analytical C-18 column, 33 mm×4.6 mm) at 25° C. The mobile phase was a mixture of water (0.1% TFA)/acetonitrile (0.1% TFA) with the ratio of 35/65 (v/v), 40/60 (v/v) and 57/43 (v/v) for the assay of DAF, NR and curcumin, respectively. The mobile phase was delivered at a flow rate of 1 mL/min. The UV/vis detector was set at 270, 550 and 390 nm for DAF, NR and curcumin, respectively. Standard calibration samples were prepared at concentrations ranging from 1 to 50 μg/mL for all solutes. The calibration curves exhibited linear behavior over the concentration range of about three orders of magnitude. The detection limits were evaluated on the basis of a signal to noise ratio of 3 and were 0.07 μg/mL for DAF and 0.04 μg/mL for NR and 0.02 μg/mL for curcumin. Intra- and inter-day precision and accuracy determination of quality control samples were better than 10% across the range of the calibration curve. In addition, the specificity was determined by comparing the results obtained in the analysis of placebo supernatant, containing only nanospheres, with those obtained in the analysis of all standard solutions of the solutes and no interference from nanospheres was observed.

To determine the solute binding efficiency, a predetermined aliquot of the purified nanosphere-solute complex suspension was withdrawn and freeze-dried, and the dry residue was accurately weighted before thoroughly dissolving in the extraction solvent. In case of nanospheres containing either DAF or curcumin, lyophilized complexes were dissolved in 5 mL of MeOH (extracting solvent) and vigorously vortexed for 1 hour. In case of NSP-NR, the dye was extracted by dissolving the lyophilized complexes in EtOH. Solutes complexation by the nanospheres was characterized by the following ratio:

$$\text{Binding Efficiency}(\%) = \frac{\text{mass of drug in the nanospheres}}{\text{mass of drug in the feed}}$$

Solutions of each solute in propylene glycol (PG) were prepared by stirring an excess of the molecule in PG at room temperature for 24 h. The samples were filtered through 0.22%μm PVDF syringe filters (Millipore, Bedford, Mass.), and the filtrates were used for all subsequent characterizations and experiments. For passive permeation experiments, the equal concentration (confirmed using RP-HPLC) of all solutes in both PG and nanospheres was achieved by subsequent dilution of either PG-solute solution with PG or NSP-solute formulation with PBS.

Example 3

Skin Permeation Tests

Using the lipophilic model dye and applying image analysis, we investigated the potential of these nanospheres to overcome percutaneous penetration barriers. The fluorophors of choice (FIG. 1) were DAF and Nile Red, which have been previously used for visualizing of micelle and liposome distribution within the skin. The selection of curcumin was based on its inherent fluorescence and proposed potential in therapeutic combination against the melanoma. A binding efficiency of 65% of all solutes with nanospheres was obtained regardless of the extent of the solute hydrophobicity and solutes' molecular weight. The final concentration of solutes in nanospheres solutions was 180 µg/mL for DAF, 190 µg/mL for curcumin and 200 µg/mL for NR; hence ~0.02% nanosphere-solute formulations or PG-solute solutions were used in permeation studies providing sufficiently strong signal to be detected by fluorescent microscopy.

Human skin: The full thickness dermatomed (~500 µm) human skin derived from the abdominal regions of female Caucasian cadavers were obtained from AlloSource (Englewood, Colo.) and stored at −80° C. Just before each experiment, the skin was allowed to thaw to room temperature and then used immediately for in vitro transport studies.

Transport studies: Pieces of full thickness human skin were mounted on Franz diffusion cells (PermeGear, Bethlehem, Pa.), exhibiting a diffusion surface area of 0.64 $cm^2$. The receptor compartments were filled with 0.155 M phosphate buffered saline (pH 7.4, 5.1 mL), which was stirred at 600 rpm. The fluid in each receptor compartment was maintained at 37±0.5° C. by the use of a thermostatic water pump (Haake DC10, Karlsruhe, Germany) that circulated water through the jacket surrounding each main chamber. Under these conditions, the temperature at the skin surface was 32±0.5° C. The skins were initially left in the Franz cells for 1 h in order to facilitate hydration of the membranes.

After this period, 0.3 mL of the appropriate formulation of solutes (in NSP or PG) was deposited on to the surface of each skin sample for 1, 3, 6 and 24 hours in case NR permeation experiments and 24 hours for DAF and curcumin permeation studies. In all experiments, the donor compartment of the sampling port of each Franz cell was covered with a taught layer of Parafilm®, and the whole set up was roofed with aluminum foil to prevent the dye bleaching. Each permeation experiment was conducted in sextuplicate or quadruplicate (in case of time-dependency experiments).

At the end of the permeation experiment, the excess formulation was removed from the skin surface, skin sections were detached from the diffusion cells, washed three times with PBS, and dried gently with delicate task wipers (Kimwipes). The skins were frozen at −20° C., and 0.2×0.5 cm piece from the treated area was cut out and imbedded in optimal cutting temperature compound (OCT). A cryostat (Leica Cryostat CM 3050S, Wetzlar, Germany) was used to prepare the cross-section of full skin perpendicular to the skin surface. Nine to twelve vertical sections with a thickness of 20 µm each were obtained and stored at −4° C. till analyzed microscopically.

Cutaneous uptake: In vitro passive permeation experiments involving 24 hrs topical applications of NSP-solute formulations and/or PG-solute solutions to human cadaver skin revealed that the amount of solutes in the receptor compartments was below the limit of detection. In this study, the absence of detectable permeation of all tested dyes via nanosphere delivery suggests that tyrosine-derived nanospheres do not facilitate transport across the human skin. Similar observations were previously reported using PLGA-fluorescent microparticles, which were clearly visualized within the skin layers but were not able to reach the receptor compartment of the diffusion cells. This result is in agreement with previous studies, which reported that the use of particulate drug carriers appeared to improve the drug residence in skin without increasing transdermal transport.

Fluorescent microscopy. Skin sections were subjected to both fluorescent and phase-contrast microscopy using Olympus CK40 microscope equipped with a UV source and filters for fluorescent measurement. Image capture and analysis were carried out using Olympus Microsuite™ B35V program. The excitation and emission wavelengths for DAF and curcumin were 485 and 520 nm, and 546 and 585 nm for Nile Red, respectively. Images were recorded setting the camera integration time of 500 ms. The same parameters were used for imaging all samples and no corrections for the background fluorescence were made. Fluorescence yield was quantified using the image treatment software (ImageJ, v1.36, NIH); the integration of pixel brightness values (arbitrary units, ABU) gives the relative dye content.

Figure 4:
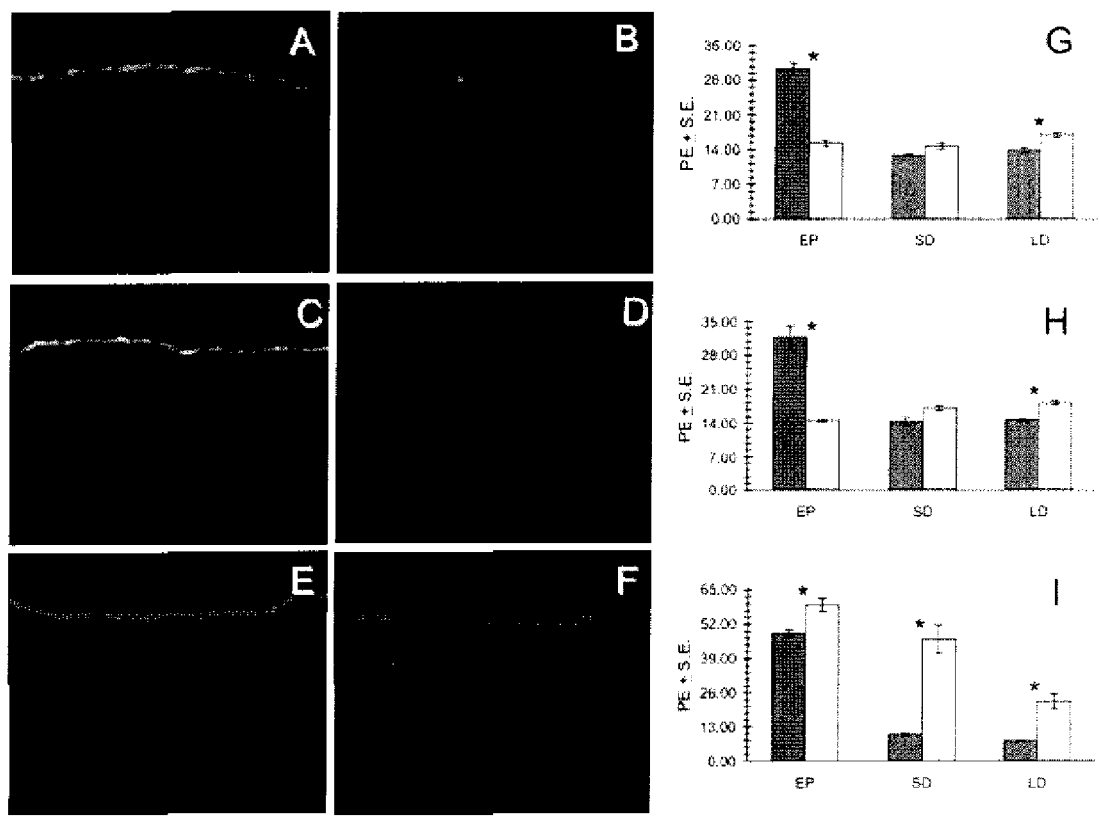
FIGS. 4A-I are cross-sectional fluorescent images obtained following 24 hrs of passive permeation. (A) PG-DAF; (B) NSP-DAF; (C) PG-curcumin; (D) NSP-curcumin; (E) PG-NR; (F) NSP-NR. Penetration effect (PE±standard error, *p<0.01) of NSP with respect to PG after 24 hrs of passive permeation. (v) PG and (□) NSP: (G) DAF; (H) curcumin; (I) NR. EP: stratum corneum and the viable epidermis; SD: superficial dermis; LD: lower dermis.

Images of the skin treated with PBS and/or tyrosine-derived nanospheres alone did not reveal any significant fluorescent signal (results not shown). FIG. 4 depicts representative examples of fluorescence microscopy images of vertically cross-sectioned human skin following topical application of DAF, curcumin and NR for 24 hrs. The visualization qualitatively indicates the most pronounced trends of fluorescence staining in skin strata: tyrosine derived nanospheres evidently enhanced penetration of dyes as compared to PG. These differences are more significant in case of NSP-NR (FIG. 4, E vs. F).

Figure 5:
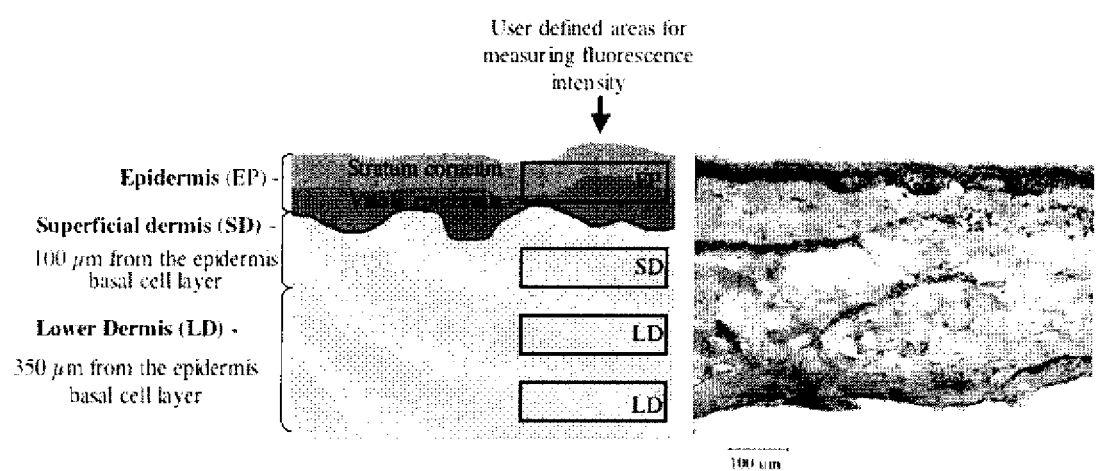
FIG. 5 is a schematic representation of cryosectioned skin (Left) and H&E staining (Right)

In addition, the nature of vehicles used affected distribution of the dye in stratum corneum. The intense fluorescence observed in this layer for all the dyes delivered via PG can be attributed to the high viscosity of this vehicle and therefore, aqueous washings could not remove excess of PG formulation from the top of the skin at the end of the experiment. Additionally, it has been suggested that increased solvent viscosity had the potential to decrease skin permeability and solute diffusion. Quantitative analysis of dye penetration into skin was obtained by calculating pixel intensities from fluorescence measurements of skin sections. Image analysis was carried out for the epidermis (EP; consisting of stratum corneum and the viable epidermis), superficial dermis (SD) and lower dermis (LD) as schematically represented in FIG. 5. The superficial dermis is defined as the region measuring around 100 µm below the epidermis and the lower dermis is the remaining portion of the dermis below the superficial dermis.

Histology of cryosectioned skin: Histology of the skin sections obtained by cryosectioning was examined using the modification of hematoxylin and eosin (H&E) staining procedure provided by the manufacturer. Briefly, skin sections were hydrated in distilled water for 1 min and then stained with Gill 2 Hematoxylin (Sigma, St. Louis, Mo.) for 4 min. Excess stain was washed off by rinsing the slides in distilled water three times, for 1 min each, followed by the addition of Scott's Solution (0.1% Sodium Bicarbonate) for 2 min. After a brief rinse in distilled water the skin sections were counterstained in acidified Eosin Y (Sigma, St. Louis, Mo.) for 3 min. Slides were sequentially dehydrated using 95% ethanol, followed by 80% and 70% ethanol (1 min each). After clearing in three changes of xylene for 1 min each, the slides containing skin sections were mounted using a Paramount mounting medium, dried overnight and analyzed microscopically.

H&E staining of the skin section (FIG. 5) was used to define the above layers for which quantitative analysis of dyes penetration was carried out. The fluorescence intensities of DAF, curcumin and NR in different layers of skin are expressed in arbitrary units (ABU) and are shown in FIG. 4 (G-I).

After 24 hrs of application, the penetration of DAF and curcumin in different layers of skin showed a very similar pattern, where the fluorescence in epidermis from PG-dye (PE value of 30.3±1.2 and 31.6±2.5 for DAF and curcumin, respectively) was significantly higher than that with NSP-dye formulations (PE of 15.3±0.8 and 14.5±0.2 for DAF and curcumin, respectively, $p<0.01$). The dye distribution in superficial and lower dermis was not significantly different (p>0.01) for both DAF and curcumin regardless how they were delivered (FIG. 4). The observed lower than expected fluorescence of DAF and curcumin delivered by NSP, particularly in SD and LD, can be attributed to the fluorescence quenching effects of the nanospheres.

However, in case of NR, the fluorescence distribution showed a totally different pattern (FIGS. 4 (E, F, I)). When applied using nanospheres, Nile Red concentrations in EP, SD and LD were significantly higher than those delivered using PG, with about fourfold and threefold increase in SD and LD, respectively. A minor, yet significant improved penetration of NSP-NR was also seen in EP with PE values of 48.6±1.3 and 59.4±2.5, for PG and nanospheres, respectively.

Figure 6:
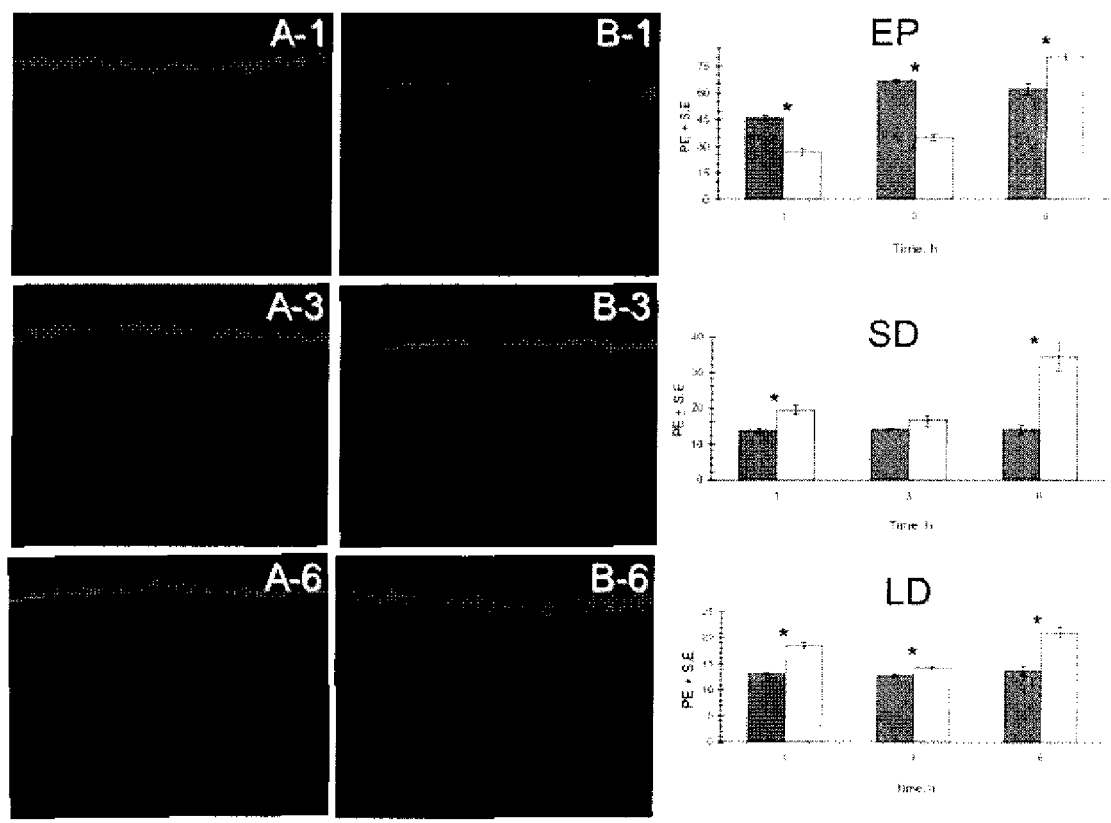
FIGS. 6A-B are cross-sectional images obtained following 1, 3 and 6 hrs of passive permeation. (A) PG-NR; (B) NSP-NR. Penetration effect (PE±standard error, *p<0.01) of NSP with respect to PG after 1, 3, and 6 hrs of passive permeation. (v) PG-NR and (□) NSP-NR: EP: stratum corneum and the viable epidermis; SD: superficial dermis; LD: lower dermis.

Interestingly, the penetration of all dyes in PG extended beyond EP into the dermis, where the decrease was about two and a half fold for DAF and curcumin and about five fold for NR (FIG. 4(G-I)). On the other hand, the PE of nanospheres resulted in an increase in dye penetration from EP to LD for DAF and curcumin, while for NR, the fluorescence intensities from NSP-dye formulations showed a 2.5 fold decrease from EP to LD. Due to the possible quenching of DAF and curcumin fluorescence by the nanospheres, we suspect that some of the fluorescence intensities of NSP-DAF and NSP-curcumin in EP and SD strata were masked. Thus, in this study we consider the results obtained with NR as more accurate in describing the nanosphere delivery potential. FIG. 6 generally supports the fact that the efficiency of skin permeation of all hydrophobic solutes delivered via nanospheres was equal or more than delivered with propylene glycol.

An additional aspect was obtained from comparison of the time dependence of dye permeation following NSP and PG application (FIG. 6). After 1 hr application of respective samples (FIGS. 6, A-1 and B-1), significance difference in the fluorescence intensity was detected in EP for skin treated with PG-NR and NSP-NR, while no difference in dye distribution was seen in lower skin layers (SD & LD) for both. The measured PE values in control sample (PG) of 45.9 in EP and 13.3 in both SD and LD as compared to 26.6 in EP and 18.9 in both SD and LD suggest that nanosphere diffusion into lower layers of skin is about 60% more than that of PG during the first hour (FIG. 6). This implies that the tyrosine-derived nanospheres are not just capable of delivering hydrophobic compounds in to the skin, but also the therapeutic dose can be achieved in a much shorter time. After 6 hrs (FIGS. 6, A-6 and B-6) of application of NR in both formulations, increased fluorescence intensity was observed in all layers of skin; furthermore, the fluorescence also persisted to a greater depth in case of NSP-NR. The PE values range from 13.9±1.1 and 13.7±0.9 for PG-NR and 34.4±4.0 and 21±1.1 for NSP-NR in SD and LD, respectively. These numbers translate to about 40% increase in NSP-NR diffusion in SD, as compared to about 10% increase in LD.

In vitro evaluation of nanosphere-curcumin formulation: Biological activity of free and nanosphere-curcumin complexes was determined using human melanoma B16 cells. Serial dilutions of the free curcumin (in DMSO) and purified nanosphere-curcumin formulation were added to the B16 cells, and the cells were grown at 37° C./5% $CO_2$. Following three days of growth, the concentration required for 50% cell growth inhibition (LC50) was determined indirectly by an MTS assay following conditions described by the manufacturer (CellTiter 96 Aqueous One Solution Cell Proliferation Assay; Promega Corp., Madison, Wis.). Comparisons of the LC50's of purified nanospheres to free curcumin provided an indication of the effect of the nanospheres on curcumin activity.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

What is claimed is:

1. A topical composition comprising: (a) an active compound for topical delivery through the stratum corneum, wherein said active compound is complexed with nanospheres of a triblock copolymer having an A-B-A structure wherein each A end block is a poly(alkylene oxide) and the middle B block is a hydrophobic polymer or oligomer with the same or different repeating units having a structure according to the formula:

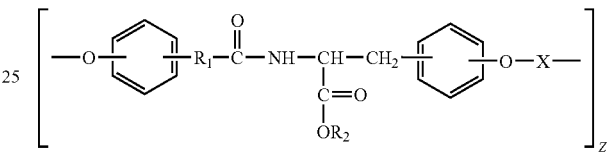

wherein X is

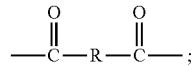

Z is a number between 2 and about 100, inclusive that provides a middle block with a weight-average molecular weight between about 1000 and about 25,000 g/mol; $R_1$ is CH=CH or $(CH_2)_n$ wherein n is from 0 to 18, inclusive; $R_2$ is selected from the group consisting of hydrogen and straight and branched alkyl, benzyl, alkylaryl and alkoxyaryl groups containing up to 18 carbon atoms; and R is selected from the group consisting of a bond and straight and branched alkylene, alkoxylene, alkylarylene and alkoxyarylene groups containing up to 18 carbon atoms, wherein m for each A is independently selected to have a weight-average molecular weight between about 1000 and about 15,000 g/mol; and (b) a pharmaceutically acceptable carrier for topical delivery.

2. The topical composition of claim 1, wherein said pharmaceutically acceptable carrier comprises one or more ingredients selected from the group consisting of diluents, solubilizers, lubricants, suspending agents, encapsulating materials, solvents, thickeners, dispersants, buffers, anti-oxidants, preservatives, carbohydrates, sugars, chelating agents, sugar alcohols, counter-ions and non-ionic surfactants.

3. The topical composition of claim 2, wherein said pharmaceutically acceptable carrier is formulated as an aqueous dispersion, emulsion, cream, ointment, gel-like matrix, solid polymer matrix, or porous ceramic matrix.

4. The topical composition of claim 1, wherein said active compound is hydrophilic.

5. The topical composition of claim 1, wherein said active compound is hydrophobic.

6. The topical composition of claim 1, wherein said active compound is a systemic drug.

7. The topical composition of claim 1, wherein said active compound is a local drug.

8. The topical composition of claim 1, wherein said active compound comprises at least one compound selected from the group consisting of antibiotics, anti-acne agents, anti-tumor agents, non-steroidal anti-inflammatory agents (NSAIDs), antihistaminic agents, antitussive agents, antipruritic agents, anticholinergic agents, anti-emetic and antinauseant agents, anorexic agents, central stimulant agents, antiarrhythmic agents, β-adrenergic blocker agents, cardiotonic agents, antihypertensive agents, diuretic agents, vasodilator agents, vasoconstrictor agents, anti-ulcer agents, anesthetic agents, antidepressant agents, tranquilizer and sedative agents, antipsychotic agents, antimicrobial agents, antineoplastic agents, antimalarial agents, muscle relaxant agents and antidiarrheal agents.

9. The topical composition of claim 1, wherein said active compound comprises one or more therapeutic agents for the treatment of a skin disease or disorder selected from the group consisting of parasitic infections, fungal infections, bacterial infections, viral infections, papulosquamous diseases, pigmentary disorders, cancers and cutaneous drug reactions.

10. The topical composition of claim 1, further comprising a dermal penetration enhancer.

11. The topical composition of claim 10, wherein said dermal penetration enhancer is selected from the group consisting of fatty acids, fatty acid esters, fatty alcohols, terpenes, glycols, glycol esters, 1,3-dioxolanes, macrocyclic ketones containing at least 12 carbon atoms, oxazolidinones, and oxazolidinone derivatives, alkyl-2-(N,N-disubstituted amino)-alkanoate esters, (N,N-disubstituted amino)-alkanol alkanoates and mixtures of two or more thereof.

12. The topical composition of claim 11, wherein said dermal penetration enhancer is selected from the group consisting of oleic acid, oleyl alcohol, cyclopenta-decanone, sorbitan monooleate, glycerol monooleate, propylene glycol monolaurate, poly-ethylene glycol monolaurate, 2-n-nonyl 1,3-dioxolane, dodecyl 2-(N,N-dimethylamino) propionate (DDAIP), DDAIP salts, 2-ethylhexyl 2-ethyl-hexanoate, isopropyl myristate, dimethyl isosorbide, 4-decyloxazolidinon-2-one, 3-methyl-4-decyloxazolidinon-2-one, octyl dimethyl-paraaminobenzoate, octyl paramethoxy-cinnamate, octyl salicylate and mixtures of two or more thereof.

13. A topical method of active compound delivery through the stratum corneum to the underlying epidermis and dermis comprising topically applying to the stratum corneum of a patient with a disease or disorder in need of treatment an effective amount of the topical composition of claim 1, wherein the active compound of said topical composition is effective to treat the disease or disorder of said patient.

14. The method of claim 13, wherein said active compound comprises at least one compound selected from the group consisting of antibiotics, anti-acne agents, anti-tumor agents, non-steroidal anti-inflammatory agents (NSAIDs), antihistaminic agents, anti-tussive agents, antipruritic agents, anticholinergic agents, anti-emetic agents, antinauseant agents, anorexic agents, central stimulant agents, antiarrhythmic agents, β-adrenergic blocker agents, cardiotonic agents, antihypertensive agents, diuretic agents, vasodilator agents, vasoconstrictor agents, anti-ulcer agents, anesthetic agents, anti-depressant agents, tranquilizer agents, sedative agents, antipsychotic agents, antimicrobial agents, antineoplastic agents, antimalarial agents, muscle relaxant agents and antidiarrheal agents.

15. The method of claim 13, wherein said disease or disorder is a skin disease or disorder selected from the group consisting of parasitic infections, fungal infections, bacterial infections, viral infections, papulosquamous diseases, pigmentary disorders, cancers and cutaneous drug reactions and said active compound comprises one or more therapeutic agents for the treatment of said skin disease or disorder.

16. The method of claim 13, wherein said active compound is delivered systemically.

17. The method of claim 13, wherein said active compound is delivered locally.

18. The method of claim 13, wherein said pharmaceutically acceptable carrier comprises one or more ingredients selected from the group consisting of diluents, solubilizers, lubricants, suspending agents, encapsulating materials, solvents, thickeners, dispersants, buffers, anti-oxidants, preservatives, carbohydrates, sugars, chelating agents, sugar alcohols, counter-ions and non-ionic surfactants.

19. The method of claim 18, wherein said pharmaceutically acceptable carrier is formulated as an aqueous dispersion, emulsion, cream, ointment, gel-like matrix, solid polymer matrix, or porous ceramic matrix.

20. The method of claim 13, wherein said topical composition further comprises a dermal penetration enhancer.

21. The method of claim 20, wherein said dermal penetration enhancer is selected from the group consisting of fatty acids, fatty acid esters, fatty alcohols, terpenes, glycols, glycol esters, 1,3-dioxolanes, macrocyclic ketones containing at least 12 carbon atoms, oxazolidinones, oxazolidinone derivatives, alkyl-2-(N,N-disubstituted amino)-alkanoate esters, (N,N-disubstituted amino)-alkanol alkanoates and mixtures of two or more thereof.

22. The method of claim 13, wherein said method further comprises applying said topical composition in combination with a physical method for enhancement of skin delivery.

23. The method of claim 22, wherein said physical enhancement method is selected from the group consisting of thermal energy methods, ultrasound methods, magnetophoresis methods, photochemical wave methods, laser ablation methods, radio frequency energy methods, pulsed electric field methods, electrophoresis methods, iontophoresis methods, microscissioned microconduit methods, membrane electroporation methods, solid microneedle methods, hollow microneedle methods, puncture methods, perforation methods, abrasion methods, needle-less injection methods, suction methods and stretching methods.

24. A hydrogel for topical application formed from the topical composition of claim 1.

25. A transdermal drug delivery device comprising an active compound depot formed from the hydrogel of claim 24.

26. The transdermal drug delivery device of claim 25, wherein said hydro-gel further comprises a dermal penetration enhancer.

27. The method of claim 13, wherein said topical composition is in the form of a hydrogel.

28. The method of claim 27, wherein said hydrogel is the active compound depot of a transdermal drug delivery device.

29. The method of claim 27, wherein said hydrogel further comprises a dermal penetration enhancer.

30. The method of claim 29, wherein said dermal penetration enhancer is selected from the group consisting of fatty acids, fatty acid esters, fatty alcohols, terpenes, glycols, glycol esters, 1,3-dioxolanes, macrocyclic ketones containing at least 12 carbon atoms, oxazolidinones, oxazolidinone derivatives, alkyl-2-(N,N-disubstituted amino)-alkanoate esters, (N,N-disubstituted amino)-alkanol alkanoates and mixtures of two or more thereof.

31. The topical composition of claim 1, wherein said active compound comprises at least one compound selected from the group consisting of antibiotics, anti-tumor agents, anti-inflammatory agents, antimicrobial agents and antineoplastic agents.

32. The method of claim 13, wherein said active compound comprises at least one compound selected from the group consisting of antibiotics, anti-tumor agents, anti-inflammatory agents, antimicrobial agents and antineoplastic agents.

33. A method for treating melanoma, comprising topically applying to the melanoma tumor of a patient in need of treatment an effective amount of the topical composition of claim 1, wherein the active compound of said topical composition comprises an antineoplastic or anti-tumor agent effective against melanoma, optionally in combination with an active compound selected from the group consisting of antibiotics, antimicrobial agents and anti-inflammatory agents.

34. A hydrogel for topical application formed from the topical composition of claim 31.

35. The method of claim 15, wherein the cancer comprises melanoma.

\* \* \* \* \*

UNITED STATES PATENT AND TRADEMARK OFFICE
CERTIFICATE OF CORRECTION

| | | |
|---|---|---|
| PATENT NO. | : 8,414,871 B2 | Page 1 of 2 |
| APPLICATION NO. | : 12/525529 | |
| DATED | : April 9, 2013 | |
| INVENTOR(S) | : Joachim Kohn et al. | |

It is certified that error appears in the above-identified patent and that said Letters Patent is hereby corrected as shown below:

On the Title Page:

Item [54] and in the Specification, Column 1, In the Title:

Replace the title

"CONTROLLED RELEASES OF ACTIVES IN SKIN"

with

--CONTROLLED RELEASE OF ACTIVES IN SKIN--

Item [57], In the Abstract:

Replace the following in the abstract, line 8,

"wherein X is —C—R—C— or —C—; Z is between 2 and about 100, inclusive; $R_1$ is CH=CH or ($CH_2$), wherein n is from 0 to 18, inclusive;"

with

--wherein X is —C(=O)—R—C(=O)— or —C(=O)—; Z is between 2 and about 100, inclusive; $R_1$ is CH=CH or $(CH_2)_n$, wherein n is from 0 to 18, inclusive--

In the Claims:

At column 20, line 46, delete the following from claim 1:

"m for" in the phrase "...wherein m for each A is independently selected..."

so that the claim reads:

--...wherein each A is independently selected....-- as follows:

--1. A topical composition comprising: (a) an active compound for topical delivery through the stratum corneum, wherein said active compound is complexed with nanospheres of a triblock Signed and Sealed this
Eighteenth Day of February, 2014

Michelle K. Lee
*Deputy Director of the United States Patent and Trademark Office* copolymer having an A-B-A structure wherein each A end block is a poly(alkylene oxide) and the middle B block is a hydrophobic polymer or oligomer with the same or different repeating units having a structure according to the formula:

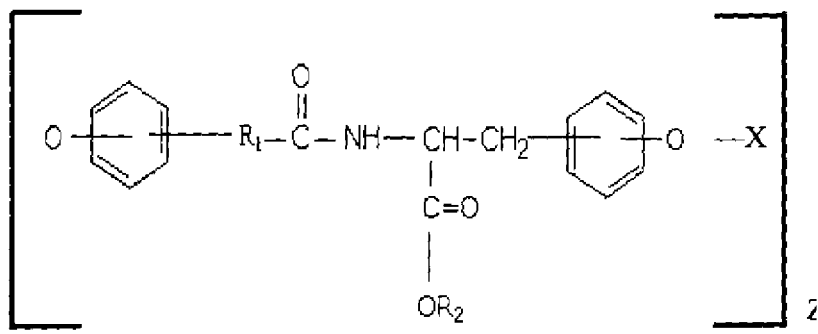

wherein X is ; Z is a number between 2 and about 100, inclusive that provides a middle block with a weight-average molecular weight between about 1000 and about 25,000 g/mol; $R_1$ is CH=CH or $(CH_2)_n$ wherein n is from 0 to 18, inclusive; $R_2$ is selected from the group consisting of hydrogen and straight and branched alkyl, benzyl, alkylaryl and alkoxyaryl groups containing up to 18 carbon atoms; and R is selected from the group consisting of a bond and straight and branched alkylene, alkoxylene, alkylarylene and alkoxyarylene groups containing up to 18 carbon atoms, wherein ~~m for~~ each A is independently selected to have a weight-average molecular weight between about 1000 and about 15,000 g/mol; and (b) a pharmaceutically acceptable carrier for topical delivery.--